(12) United States Patent
Kump et al.

(10) Patent No.: US 7,342,998 B2
(45) Date of Patent: Mar. 11, 2008

(54) X-RAY DETECTOR QUICK-CONNECT CONNECTION SYSTEM

(75) Inventors: Kenneth Kump, Waukesha, WI (US); Michael J. Utschig, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 207 days.

(21) Appl. No.: 10/904,612

(22) Filed: Nov. 18, 2004

(65) Prior Publication Data

US 2006/0104416 A1     May 18, 2006

(51) Int. Cl.
*H05G 1/08*     (2006.01)

(52) U.S. Cl. .......................................... 378/91; 378/204

(58) Field of Classification Search .................. 378/19, 378/91, 98.8, 116, 204; 250/370.08, 370.09, 250/580
See application file for complete search history.

(56) References Cited

U.S. PATENT DOCUMENTS

| | | | |
|---|---|---|---|
| 5,103,092 A | 4/1992 | Takahashi et al. | 250/252.1 |
| 5,262,871 A | 11/1993 | Wilder et al. | 348/307 |
| 5,281,803 A | 1/1994 | Ishizuka | 250/208.1 |
| 5,508,740 A | 4/1996 | Miyaguchi et al. | 348/244 |
| 5,514,873 A | 5/1996 | Schulze-Ganzlin et al. | 250/394 |
| 5,608,774 A * | 3/1997 | Polichar et al. | 378/98.8 |
| 5,661,309 A | 8/1997 | Jeromin et al. | 250/580 |
| 5,693,948 A | 12/1997 | Sayed et al. | 250/370.09 |
| 5,715,292 A | 2/1998 | Sayag et al. | 378/98.8 |
| 5,773,832 A | 6/1998 | Sayed et al. | 250/370.09 |
| 5,811,790 A | 9/1998 | Endo et al. | 250/208.1 |
| 5,828,726 A | 10/1998 | Polichar et al. | 378/98.2 |
| 5,903,052 A | 5/1999 | Chen et al. | 257/706 |
| 5,909,478 A | 6/1999 | Polichar et al. | 378/98.2 |
| 5,962,856 A | 10/1999 | Zhao et al. | 250/370.09 |
| 5,965,872 A | 10/1999 | Endo et al. | 250/208.1 |
| 6,049,074 A | 4/2000 | Endo et al. | 250/208.1 |
| 6,127,714 A | 10/2000 | Mochizuki | 257/443 |
| 6,208,708 B1 | 3/2001 | Hoheisel et al. | 378/37 |
| 6,232,607 B1 | 5/2001 | Huang | 250/370.09 |
| 6,239,439 B1 | 5/2001 | Itabashi et al. | 250/370.11 |
| 6,255,638 B1 | 7/2001 | Eräluoto et al. | 250/208.1 |
| 6,323,891 B1 | 11/2001 | Kitani et al. | 347/263 |
| 6,331,705 B1 | 12/2001 | Eisen et al. | 250/370.01 |
| 6,333,963 B1 | 12/2001 | Kaifu et al. | 378/98.2 |

(Continued)

FOREIGN PATENT DOCUMENTS

JP     11271454     10/1999

(Continued)

*Primary Examiner*—Courtney Thomas
(74) *Attorney, Agent, or Firm*—Ziolkowski Patent Solutions Group, SC (57) ABSTRACT

An x-ray system quick-connect connection is disclosed to allow an end-user to de-couple a portable x-ray detector from an x-ray scanner/host. The quick-connect connection is accessible by the end-user without removal of a service panel that exposes an interior service portion of the x-ray scanner or x-ray detector. The de-coupled x-ray detector may be stored independently from the x-ray scanner/host and may be shared among multiple x-ray scanner/host systems, when properly calibrated. De-coupling a single quick-connect connection de-couples all power and communication lines between the x-ray scanner/host and the x-ray detector.

34 Claims, 6 Drawing Sheets

U.S. PATENT DOCUMENTS

| | | | |
|---|---|---|---|
| 6,344,652 B1 | 2/2002 | Shoji | 250/370.09 |
| 6,398,409 B1 | 6/2002 | Brooks | 378/209 |
| 6,459,132 B1 | 10/2002 | Mochizuki | 257/443 |
| 6,469,312 B2 | 10/2002 | Agano | 250/580 |
| 6,475,824 B1 | 11/2002 | Kim | 438/66 |
| 6,552,319 B2 | 4/2003 | Pyyhtiä et al. | 250/208.1 |
| 6,667,480 B2 | 12/2003 | Kajiwara et al. | 360/31 |
| 6,700,126 B2 | 3/2004 | Watanabe | 250/370.09 |
| 6,707,880 B2 | 3/2004 | Yamayoshi | 378/92 |
| 6,714,623 B2 | 3/2004 | Sako et al. | 378/98.8 |
| 6,723,592 B2 | 4/2004 | Shih | 438/197 |
| 2002/0005490 A1 | 1/2002 | Watanabe | 250/370.09 |
| 2002/0150214 A1 | 10/2002 | Spahn | 378/189 |
| 2002/0181659 A1 | 12/2002 | Watanabe et al. | 378/189 |
| 2003/0031296 A1 | 2/2003 | Hoheisel | 378/98.8 |
| 2004/0146142 A1* | 7/2004 | Maijala | 378/102 |

FOREIGN PATENT DOCUMENTS

| | | |
|---|---|---|
| JP | 2001099942 | 4/2001 |
| JP | 2001198116 | 7/2001 |
| JP | 2001224579 | 8/2001 |
| JP | 2002006049 | 1/2002 |
| JP | 2002014170 | 1/2002 |
| JP | 2002048873 | 2/2002 |
| JP | 2002125960 | 5/2002 |
| JP | 2002131437 | 5/2002 |
| JP | 2003000586 | 1/2003 |
| JP | 2003010175 | 1/2003 |
| JP | 2003014862 | 1/2003 |
| JP | 2003060181 | 2/2003 |
| JP | 2003334184 | 11/2003 |

* cited by examiner

X-RAY DETECTOR QUICK-CONNECT CONNECTION SYSTEM

BACKGROUND OF THE INVENTION

The present invention relates generally to radiographic detectors and, more particularly, to an x-ray detector that may be quickly detached from an x-ray scanner when not in use.

X-ray imaging is a non-invasive technique to capture images of medical patients for clinical diagnosis as well as inspect the contents of sealed containers, such as luggage, packages, and other parcels. To capture these images, an x-ray source irradiates a scan subject with a fan beam of x-rays. The x-rays are then attenuated as they pass through the scan subject. The degree of attenuation varies across the scan subject as a result of variances in the internal composition of the subject. The attenuated energy impinges upon an x-ray detector designed to convert the attenuating energy to a form usable in image reconstruction. A control system reads out electrical charge stored in the x-ray detector and generates a corresponding image. For a conventional, screen film detector, the image is developed on a film and displayed using a backlight.

Increasingly, flat panel, digital x-ray detectors are being used to acquire data for image reconstruction. Flat panel detectors are generally constructed as having a scintillator, which is used to convert x-rays to visible light that can be detected by a photosensitive layer. The photosensitive layer includes an array of photosensitive or detection elements that each store electrical charge in proportion to the light that is individually detected. Generally, each detection element has a light sensitive region and a region comprised of electronics to control the storage and output of electrical charge. The light sensitive region is typically composed of a photoconductor, and electrons are released in the photoconductor when exposed to visible light. During this exposure, charge is collected in each detector element and is stored in a capacitor situated in the electronics region. After exposure, the charge in each detector element is read out using logic controlled electronics.

Each detector element is conventionally controlled using a transistor-based switch. In this regard, the source of the transistor is connected to the capacitor, the drain of the transistor is connected to a readout line, and the gate of the transistor is connected to a scan control interface disposed on the electronics in the detector. When negative voltage is applied to the gate, the switch is driven to an OFF state, i.e. no conduction between the source and drain. On the other hand, when a positive voltage is applied to the gate, the switch is turned ON resulting in connection of the source to the drain. Each detector element of the detector array is constructed with a respective transistor and is controlled in a manner consistent with that described below.

Specifically, during exposure to x-rays, negative voltage is applied to all gate lines resulting in all the transistor switches being driven to or placed in an OFF state. As a result, any charge accumulated during exposure is stored in each detector element capacitor. During read out, positive voltage is sequentially applied to each gate line, one gate at a time. In this regard, only one detector element is read out at a time. A multiplexer may also be used to support read out of the detector elements in a raster fashion. An advantage of sequentially reading out each detector element individually is that the charge from one detector element does not pass through any other detector elements. The output of each detector element is then input to a digitizer that digitizes the acquired signals for subsequent image reconstruction on a per pixel basis. Each pixel of the reconstructed image corresponds to a single detector element of the detector array.

Conventional x-ray detectors are usually fixedly attached to an x-ray scanner through cables and/or wires bundled together through a tether to facilitate the supply of power to the detector and to facilitate communication therebetween. The tether cables and/or wires are typically fixed to the detector and x-ray scanner such that separation of the detector from the x-ray scanner is possible only by a qualified technician. For example, the cables and/or wires are often located behind a non-user serviceable panel, thus requiring a service call from a qualified technician to access the tether connections.

This fixed connection of an x-ray detector to an x-ray scanner across a tether has a number of drawbacks. For example, a tether can be crushed or bent as it lays exposed on the floor. In another example, the x-ray detector may become damaged if it falls onto the floor through operator mishandling or through being pulled to the floor by the fixed tether when the tether is snagged. Damage caused either to the tether or to the x-ray detector when the tether is fixed to the x-ray detector and/or x-ray scanner requires that a service call be made to request that a qualified technician replace or repair the damaged components. An end-user is typically not trained for servicing internal components of the x-ray scanner or x-ray detector and damage to sensitive components other than the tether may occur if the end-user attempts to remove a fixed tether. As a result, the x-ray detector must be removed from use until serviced, which decreases subject throughput.

Additionally, a tethered connection between the x-ray detector and x-ray scanner can increase the difficulty of positioning the x-ray detector for imaging. This is particularly problematic when the x-ray detector must be placed at an awkward angle or an x-ray is to be taken in an operation room or other sterile facility. That is, an x-ray may be required of a patient during a surgical procedure and, as is well known, it is desirable to maintain a sterile environment. The tether may not be sterile and come in contact with an otherwise sterile environment as a radiologist or other user is placing the detector for data acquisition.

Therefore, it would be desirable to design an x-ray scanner that can be easily, quickly, and repeatedly detached from an x-ray scanner.

BRIEF DESCRIPTION OF THE INVENTION

The present invention is directed to a quick-connect detachable tether for an x-ray imaging system that overcomes the aforementioned drawbacks.

A quick-connect system is disclosed that allows a quick disconnection of a portable x-ray detector from an x-ray scanner. A quick-connect connection is placed in-line with a tether such that communication and/or power signals that pass between the portable x-ray detector and x-ray scanner pass therethrough. Furthermore, the quick-connect system is placed such that access thereto is available to end-users of the x-ray imaging system. In this regard, the quick-connect system allows an end-user to disconnect the x-ray detector from the x-ray imaging system when not in use. Disconnecting the x-ray detector in this manner also allows the x-ray detector to be used by and shared between multiple x-ray scanners. In addition, tethers can be replaced without replacement of an x-ray detector, and vice versa.

Therefore, in accordance with one aspect, the invention includes an x-ray scanning system comprising an x-ray scanner having an x-ray source configured to project x-rays at a subject to be imaged. The system includes an x-ray detector configured to detect x-rays projected from the x-ray source and attenuated by the subject and a quick-connect connection detachably linking the x-ray scanner and the x-ray detector.

In accordance with another aspect of the invention, the invention includes a radiographic detector comprising a scintillator configured to convert radiographic energy to light and a detector array having a plurality of detector elements to detect light from the Scintillator. A control board is included having a plurality of electronic components to control the detector array during data acquisition and data readout. The radiographic detector further includes a quick-connect connector operationally connected to the control board and configured to detachably connect to an x-ray scanner.

According to another aspect, the present invention includes an x-ray control tether comprising a flexible housing extending from a first end to a second end and configured to enclose a plurality of wires, a communication wire enclosed in the flexible housing and configured to relay communication signals between an x-ray scanner and an x-ray detector, and a power wire enclosed in the flexible housing and configured to relay power supply signals between the x-ray scanner and the x-ray detector. The x-ray control tether also includes at least one quick-connect connector attached to an end of the flexible housing and connected to the communication wire and the power wire.

According to a further aspect of the present invention, a method of imaging a subject is disclosed. The method includes the positioning an x-ray detector disconnected from an x-ray scanner in a given scan position relative to a subject to be scanned. The method further includes the steps of connecting the x-ray detector to the x-ray scanner and then acquiring radiographic data from the subject.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The present invention will be described with respect to a quick-connect connection of at least a pair of mating quick-connect connectors that may be quickly disconnected from and connected to one another when disconnecting an x-ray scanner from and connecting the x-ray scanner to an x-ray detector. The quick-connect connectors do not require end-user access to internal sockets, plugs, junctions, and the like, located in an interior portion of an x-ray scanner/host or an x-ray detector generally accessible only by a qualified technician. Instead, the quick-connect connectors are accessible by an end-user. The quick-connect connectors, for example, may be mounted in an outside panel or attached to an external tether. Furthermore, the quick-connect connectors may include a cover to minimize interference from dust or other debris therewith or to protect the quick-connect connector from accidental damage by an end-user. Implementation of a quick-connect connection allows an x-ray detector to be stored apart from an x-ray scanner, or positioned for data acquisition free of the x-ray scanner and later connected after a desired position is reached.

The present invention makes reference to a flat panel, solid-state, indirect detection, portable digital x-ray detector for use with a mobile x-ray imaging system. However, the present invention is equivalently applicable with other types of x-ray detectors including direct detection digital detectors. Additionally, the present invention may be used with stationary or fixed room x-ray imaging systems. Further, the present application makes reference to an imaging "subject" as well as an imaging "object". These terms are not mutually exclusive and, as such, use of the terms is interchangeable and is not intended to limit the scope of the appending claims.

Figure 1:
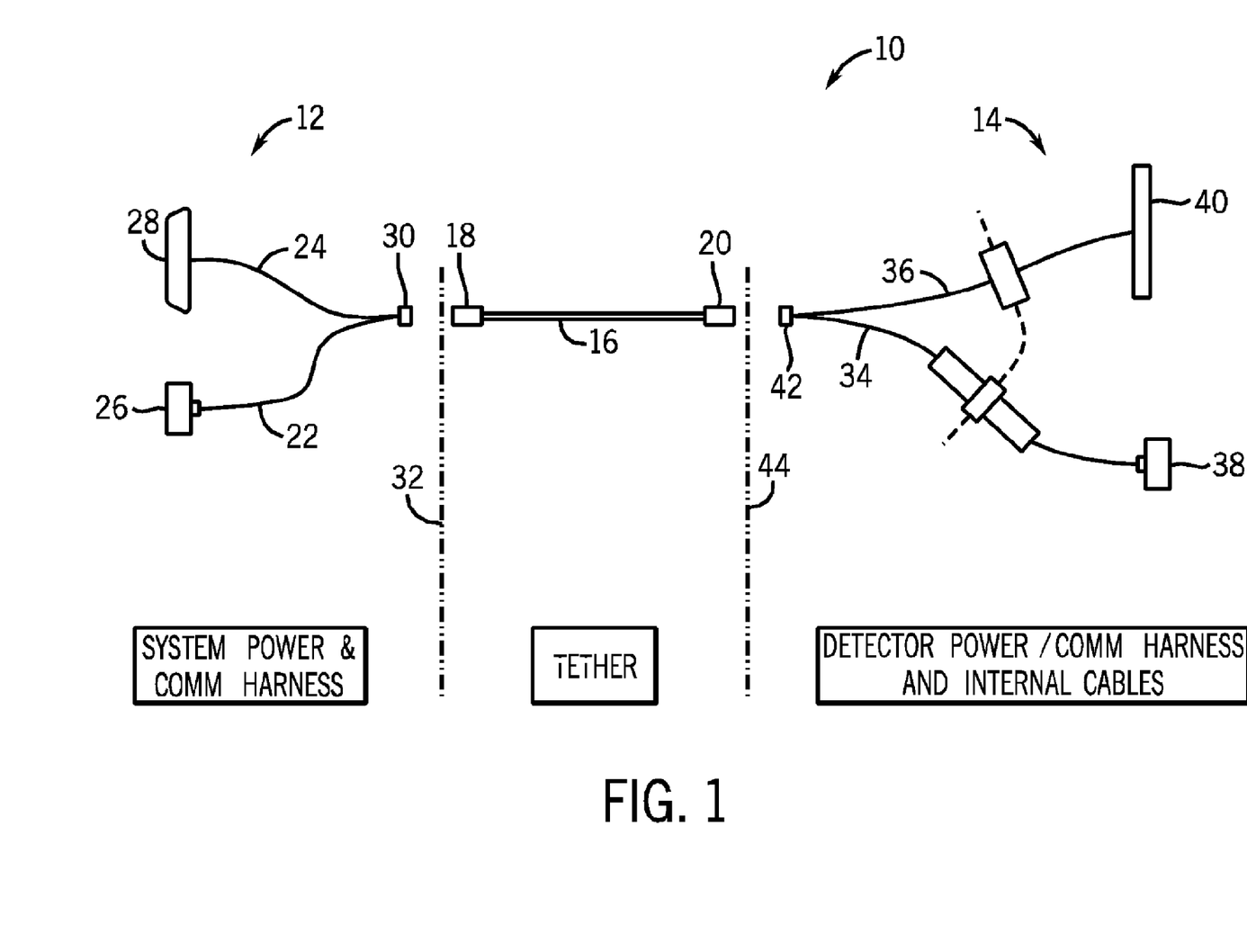
FIG. 1 is a schematic view of an x-ray imaging system in accordance with one aspect of the present invention.

Referring to FIG. 1, a schematic view shows an x-ray imaging system incorporating the present invention. X-ray imaging system 10 includes an x-ray scanner/host 12 connected to an x-ray detector 14 through a flexible tether 16. In a preferred embodiment, a pair of quick-connect connectors 18, 20 is attached to tether 16, one quick-connect connector 18, 20 attached to a respective end of tether 16. Tether 16 houses a plurality of wires attached to the pair of quick-connect connectors 18 and 20. System power wires 22 and system communication wires 24 of x-ray scanner 12 are attached at one end to control interfaces 26, 28, respectively. X-ray scanner system power wires 22 and system communication wires 24 are attached at the opposite end to quick-connect connector 30, which is preferably mounted to an external panel 32 of x-ray scanner 12 and constructed to mate with quick-connect connector 18. System power wires 34 and system communication wires 36 of x-ray detector 14 are attached at one end to control interfaces 38, 40, respectively. X-ray detector system power wires 34 and system communication wires 36 are attached at the opposite end to quick-connect connector 42, which is preferably mounted to an external panel 44 of x-ray scanner 12 constructed to mate with quick-connect connector 20.

Figure 2:
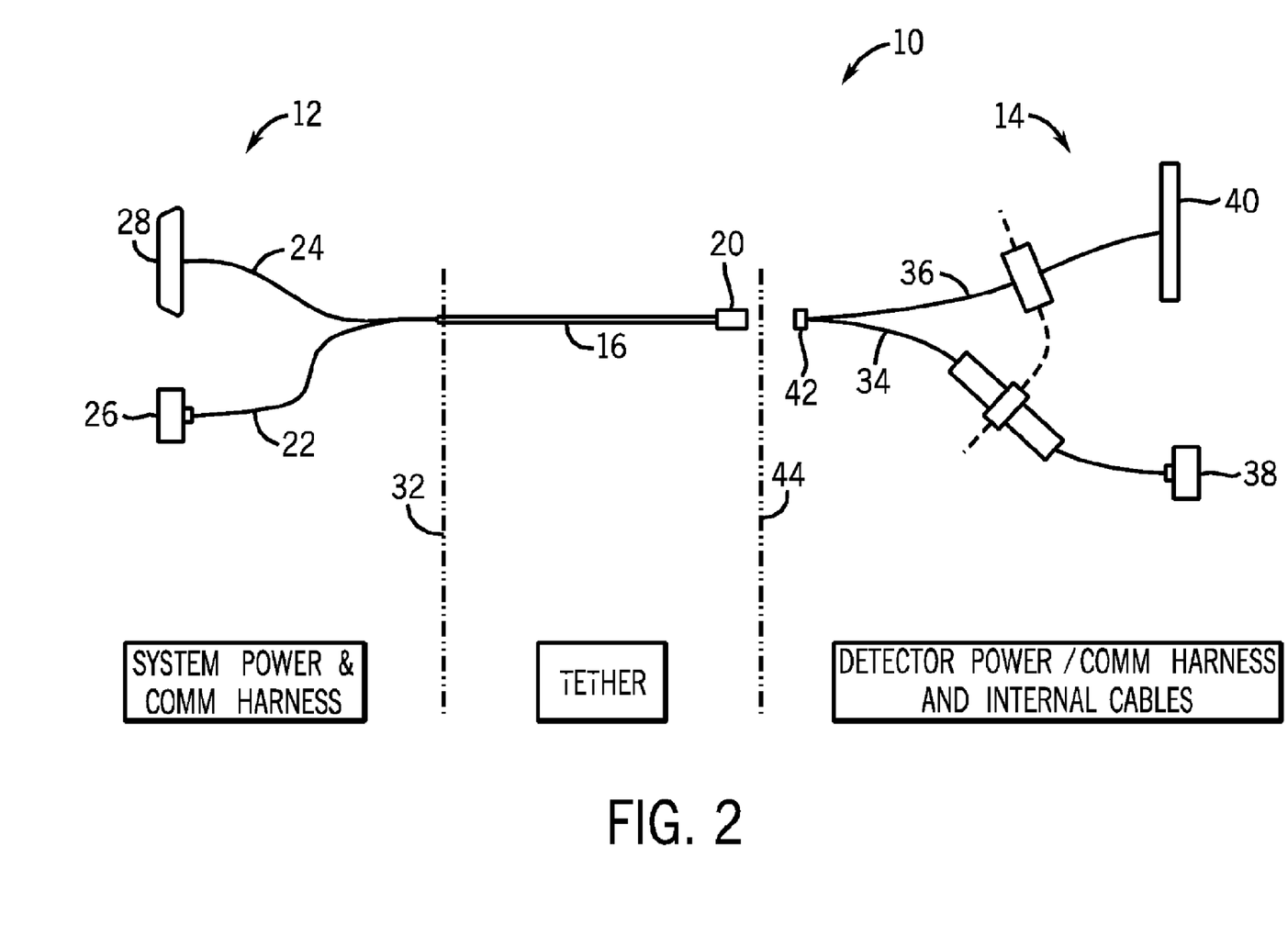
FIG. 2 is a schematic view of an x-ray imaging system in accordance with another aspect of the present invention.

Alternatively, as shown in FIG. 2, x-ray scanner power and communication wires 22, 24 extend beyond external panel 32 into tether 16 and are directly connected to quick-connect connector 20. In this manner, x-ray detector 14 may be attached to or disconnected from x-ray system 12, while tether 16 remains attached to x-ray scanner 12. In this regard, a single quick-connect connection point is formed for coupling or de-coupling x-ray scanner 12 and x-ray detector 14.

Figure 3:
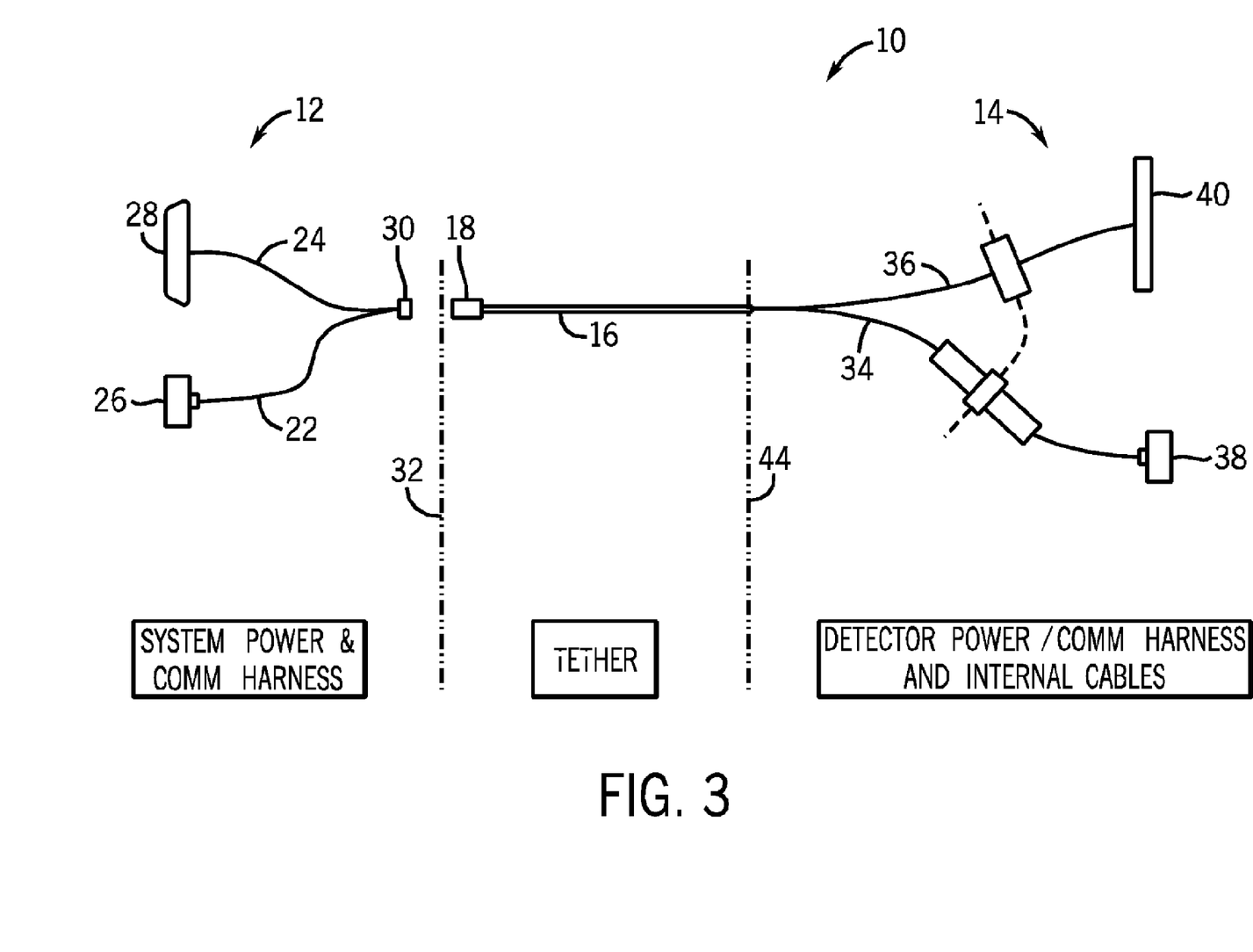
FIG. 3 is a schematic view of an x-ray imaging system in accordance with yet another aspect of the present invention.

Alternatively, as shown in FIG. 3, x-ray detector power and communication wires 34, 36 extend beyond external panel 44 into tether 16 and are directly connected to quick-connect connector 18. In this manner, x-ray detector 14 may be attached to and disconnected from x-ray system 12, while tether 16 remains attached to x-ray detector 14.

Mating quick-connect connectors are preferably designed such that one quick-connect connector has a male configuration and the other quick-connect connector has a female configuration. Furthermore, the mating quick-connect connectors are constructed to have mating pins attached to power and communication wires. The mating quick-connect connectors are coupled by aligning the quick-connect connectors and inserting one quick-connect connector into the other quick-connect connector. A secured coupling may be achieved by threadedly engaging a collar or screw attached to one quick-connect connector to threads attached to the other quick-connect connector. In addition, a latching mechanism may be used to securely connect the quick-connect connectors and prevent disconnection. In this manner, the mating quick-connect connectors cannot become de-coupled without first removing the secured engagement. Thus, inadvertent de-coupling of the quick-connect connectors may be avoided. It is also contemplated that the connectors of the tether be of a female-type and the connector of the x-ray detector and/or scanner be of the male-type, and vice versa.

Alternatively, a break-away, snap-fit, quick-connect connection may be used that supports inadvertent de-coupling of the x-ray detector or scanner from the tether. For example, a tether coupled to an x-ray detector may present a trip hazard if it lies across a path routinely traversed by personnel. If an end-user trips on the tether, the tether may become taut and damage the tether, detector, or quick-connect connection. For example, the detector may be pulled to the floor causing damage thereto. A break-away, snap-fit, quick-connect connection would mitigate damage by allowing the tether to become de-coupled from the detector when the tether is pulled away from the detector, and vice-versa.

When not in use, x-ray detector 14 may be easily detached from x-ray scanner 12 and stored remotely from the imaging system 10. It is contemplated that x-ray detector 14 may be stored in a remote docking station (not shown). The remote docking station may connect to quick-connect connector 42 of x-ray detector 14 for diagnostics tests, thermal regulation, and the like.

Figures 4, 5:
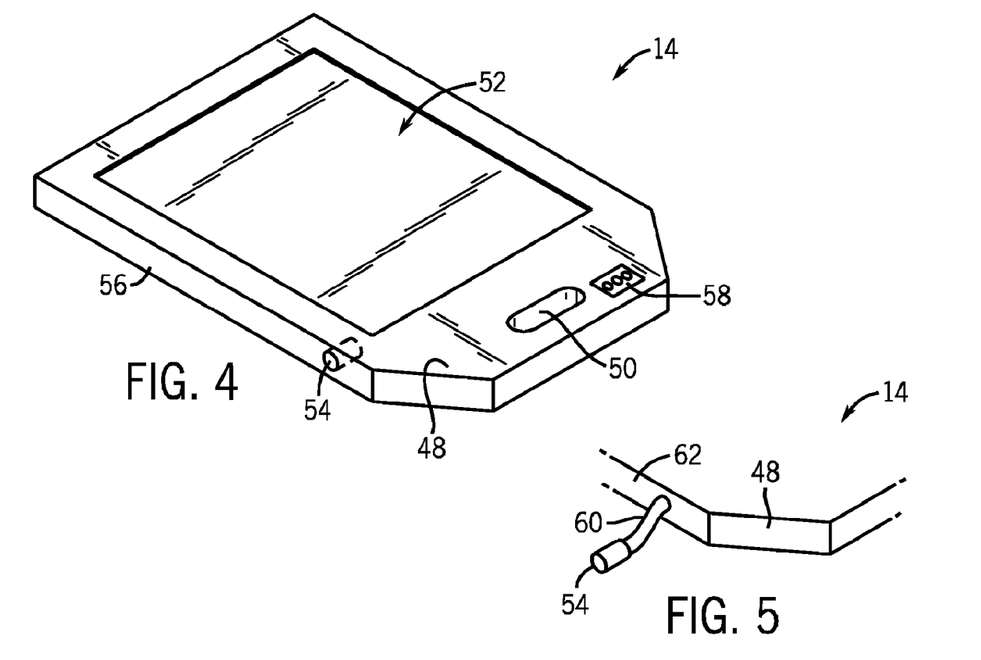
FIG. 4 is a perspective view of a portable, solid-state, flat panel, digital x-ray detector applicable with the present invention.
FIG. 5 is a perspective view of the x-ray detector of FIG. 4 according to another embodiment of the present invention.

Referring now to FIG. 4, a perspective view illustrates a flat panel, solid-state, indirect detection, portable digital x-ray detector incorporating the present invention. Detector 14 is preferably an indirect detection, solid-state, digital detector that determines x-ray attenuation through an imaging subject from the emission of light by a scintillator that emits light upon the incidence of x-rays. The detector 14 includes a cover 48 formed of lightweight, durable composite material. A handle 50 is incorporated into the cover to support the portability of the detector. The top of the cover includes a template 52 that visually defines the surface dimensions of the scintillator layer in the detector. Template 52 is designed to visually assist a user in positioning of the detector for data acquisition.

As shown in FIG. 4, detector 14 may be constructed with a quick-connect connector 54 mounted in an external surface 56 of cover 48, thus allowing access thereto by an end-user. The detector 14 may be connected to an x-ray scanner/host by coupling an end of a tether to quick-connect connector 54, the tether being connected to the x-ray scanner/host at the opposite end. Detector 14 also includes indicator lights or LEDs 58 for monitoring power status, communications status, operation, and diagnostics of the detector 14.

Alternatively, as shown in FIG. 5, quick-connect connector 54 may be attached to a tether 60 extending quick-connect connector 54 beyond cover 48 of x-ray detector 14. Thus, quick-connect connector 54 may be coupled to a mating quick-connect connector (not shown) in a plane independent of a plane formed by side 62. Tether 60 may be constructed of any length and houses power and communication wires (not shown) connecting quick-connect connector 54 to control interfaces (not shown) located within cover 48. This arrangement allows a user to position the x-ray detector free of a connection to the x-ray scanner and, after positioning the x-ray detector, connect the x-ray detector to the x-ray scanner without having to gain access to a socket or plug in the detector cover which may be difficult to access for a given patient placement.

Figure 6:
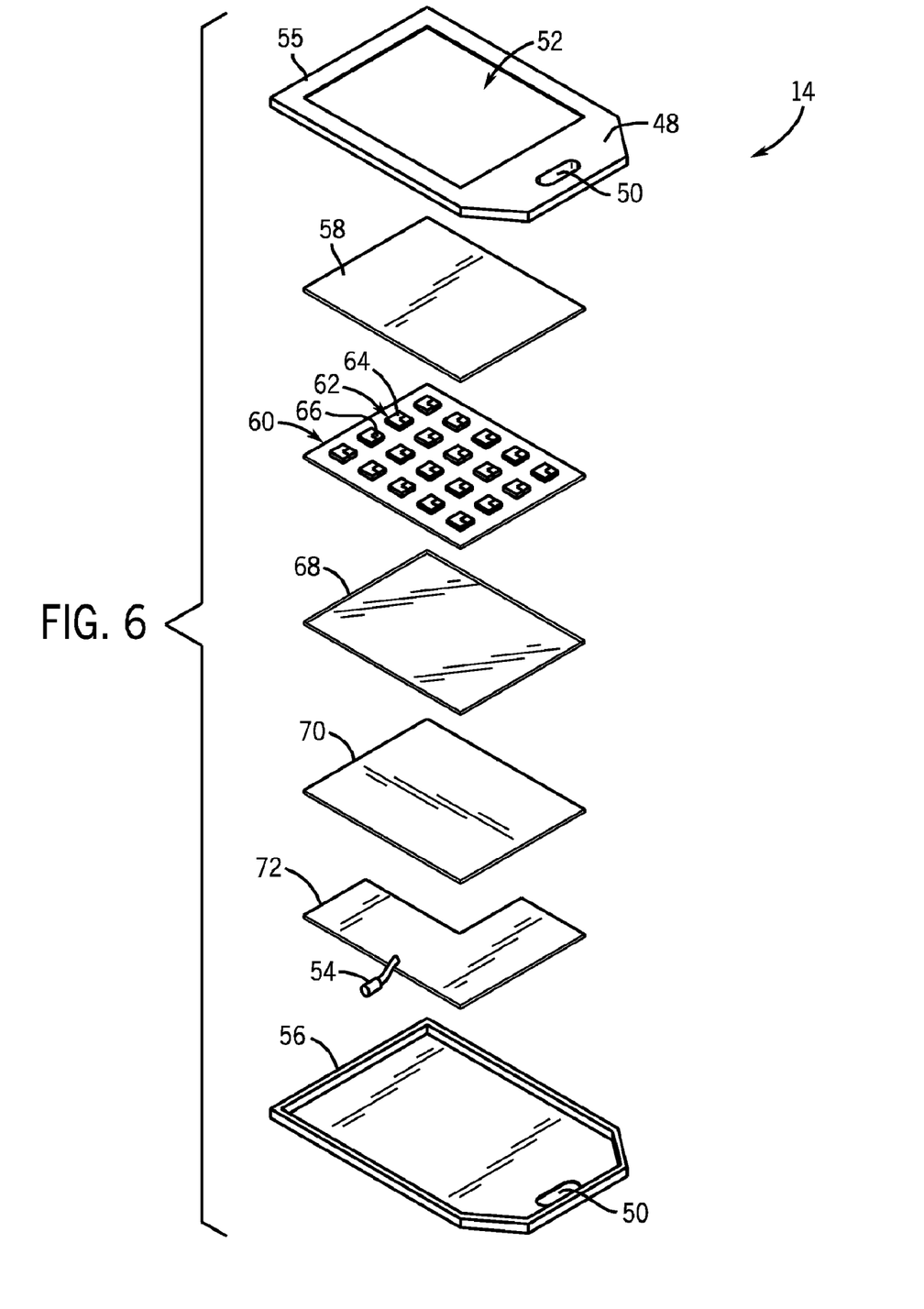
FIG. 6 is an exploded view of an x-ray detector.

Referring now to FIG. 6, an exploded view illustrates the internal composition of detector 14. Detector 14 includes a top cover 55 that along with back cover 56 provides a shell or enclosure for its internal components. Both covers 55, 56 are preferably formed of a composite material sufficient to protect the detector components from fracture when exposed to a load, e.g. 300 lbs. It is noted however that the covers may be fabricated from other materials, such as magnesium. Additionally, covers 55 and 56 may be constructed with bumpers, foam inserts, or other impact absorbing material to inhibit fracturing of the detector components when dropped. When assembled, the top cover 55 is constructed in such a manner that the detector may be placed on a floor and support a standing subject. In this regard, the top cover 55 is designed to minimally deflect when subjected to a load. Top cover 55 and back cover 56 collectively form handle 50 when assembled.

Detector 14 further includes a scintillator layer 58 designed to convert incident x-rays or gamma rays to visible light. Scintillator layer 58, which may be fabricated from CsI or other scintillating material, is designed to emit light proportional to the number and energy of the x-rays received. As such, light emissions will be higher in those regions of the scintillator layer 58 where either more x-rays were received or the energy level of the received x-rays was higher. Since the composition of the subject will attenuate the x-rays projected by the x-ray tube, the energy level of the x-rays impinging upon the scintillator layer will not be uniform across the scintillator layer. This variation in light emission will be used to capture contrast in the reconstructed image.

The light emitted by the scintillator layer 58 is detected by detector elements of a detector element array 60. Each detector element 62 corresponds to a picture element or pixel in the reconstructed image. Each detector element 62 includes a light sensitive or photoconductive region 64 and an electronics region 66. During exposure to x-rays, electrons are released in the light sensitive region 64 in proportion to the light detected in the region 64. The electronics region 66 includes a capacitor (not shown) that stores the electrical charge accumulated by the light sensitive region. After exposure, a thin-film-transistor (not shown) in the electronics region 66 is biased so as to connect the capacitor to readout electronics in the x-ray scanner. Generally, a multiplexer (not shown) is used to control read out of the discrete detector elements in a sequential, raster fashion. In this regard, the output of each detector element is sequentially input to a digitizer for digitization for subsequent image reconstruction.

The thin-film-transistors of the detector elements 62 are supported by a glass substrate 68. Lead lines (not shown) etched in substrate 68 are used for routing of the electrical output of the detector elements as well as applying the biasing voltages to the thin-film-transistors. The glass substrate is generally very thin and fragile. In this regard, as referenced above, the top cover and back cover 55 and 56 are designed with impact absorbing material to help prevent fracturing of the glass substrate. Additionally, as the detector 14 may be used to support a relatively large load during imaging, e.g. imaging of the feet of an average sized adult male, the top cover 55 is further designed to reduce the stress on the detector to further prevent fracturing of the glass substrate.

The glass substrate 68 is supported by a detector panel support 70. Panel support 70 is not only designed to support substrate 68, but is also used to separate the x-ray conversion and light detection components from the electronic control board 72. Additionally, the panel support 70 may be constructed to include radiation absorbing material in addition to structurally supporting material. Incorporating radiation absorbing material within the panel support reduces or eliminates the detection of backscattered x-rays. That is, the radiation absorbing material absorbs x-rays passing through the scintillator layer, detector element array, and glass substrate, as well as x-rays that deflect off the back cover of the detector. In this regard, the electronics 72 are not imaged.

The electronic control board 72, in one embodiment, has an L-shape and is disposed to support the processing and logic control electronics of the detector including communications to and from an x-ray scanner. The electronic control board 72 may also include temperature sensors for providing feedback as to the temperature of the detector as well as the temperature of the subject. The electronic control board 72 may also support an accelerometer designed to detect acceleration of the detector and store data accordingly. In this regard, the accelerometer may be used to record the date and time when the detector experienced dramatic increases in acceleration, i.e. when dropped. The electronic control board 72 may also include various storage devices including flash storage. The electronic control board 72 is supported by panel support and back cover 56.

Quick-connect connector 54 is attached to power and/or communication wires extending from power and communication interfaces (not shown) on electronic control board 72. Quick-connect connector 54 is constructed such that all power and/or communication signals pass therethrough. In this manner, all power and/or communication connections are connected and disconnected by coupling and de-coupling quick-connect connector 54 from a mating quick-connect connector (not shown) coupled to x-ray scanner 12. It is also contemplated that the tether may carry only power thereacross to change a battery of a wirelessly communicating x-ray detector.

Figure 7:
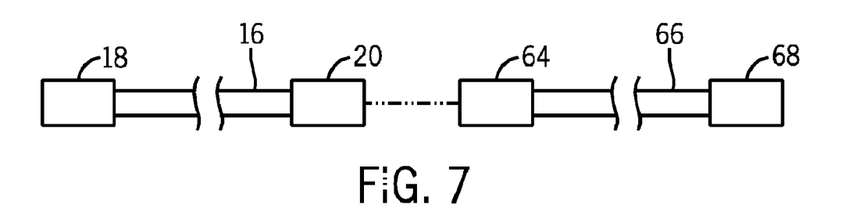
FIG. 7 is a plan view of a pair of tethers according to one embodiment of the present invention.

FIG. 7 illustrates a multitude of tethers according to one embodiment of the present invention. Quick-connect connector 20 of tether 16 may be coupled to a mating quick-connect connector 64 of an extension tether 66 to increase tether length between an x-ray scanner (not shown) coupled to quick-connect connector 68 and an x-ray detector (not shown) coupled to quick-connect connector 18. In this manner, overall tether length may be extended if needed.

Figure 8:
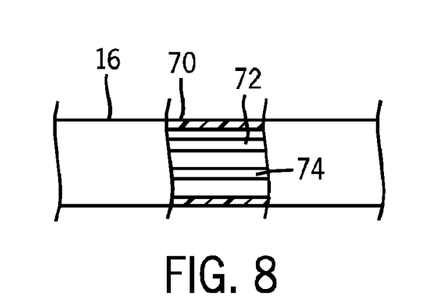
FIG. 8 is a cut-away view of the tether shown in FIG. 1.

In FIG. 8, a cut-away view of a tether is shown. Tether 16 preferably has a flexible, tubular housing 70 constructed to house one or more wires. In the preferred embodiment, a plurality of power wires 72 and/or a plurality of communication wires 74 are enclosed within housing 70 and are constructed of a metallic material such as copper. It is further contemplated that fiber optics may also be used to carry communications between the x-ray detector and scanner. Tether 16 may translate power and/or communication signals passing between an x-ray scanner and an x-ray coupled thereto.

Figure 9:
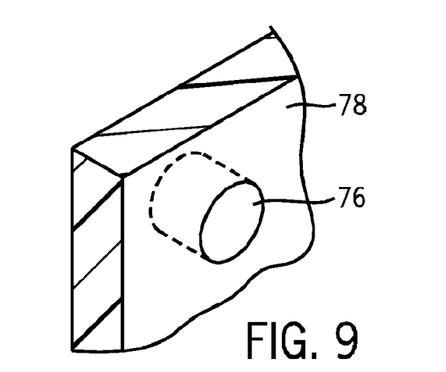
FIG. 9 is a perspective view of ax x-ray scanner wall portion incorporating the present invention.

FIG. 9 illustrates a portion of an x-ray scanner wall incorporating one embodiment of the present invention. Quick-connect connector 76 is mounted to an outside panel 78 of an x-ray scanner. Quick-connect connector 76 is configured to mate with a mating quick-connect connector (not shown) of a tether coupled to an x-ray detector such that the tether and x-ray detector may be coupled to the x-ray scanner.

It is also contemplated that a "loop-back" may be implemented to automatically detect connection of an x-ray detector to an x-ray scanner. In this regard, the quick-connect connectors may be designed to include redundant copper conductors such that pins within a connector may be shorted together when a connection is made. As such, a resistance between these two pins can be measured to detect connectivity of an x-ray detector to an x-ray scanner. For example, if an open circuit is detected, it is deemed that the x-ray scanner and x-ray detector are not connected to one another. On the other hand, a closed circuit is indicative of connection. Further, it is contemplated that based on the detected status between the x-ray scanner and x-ray detector, display messages could be provided on the x-ray scanner and/or x-ray detector. For instance, the video console of the x-ray scanner may display a "Cable is Disconnected" if an open circuit condition is detected. Feedback regarding the connection of the x-ray scanner and the x-ray detector may also be used to control power and communications systems. For example, a battery-powered x-ray detector could remain in a sleep mode until a closed circuit is detected to preserve battery life. Additionally, while it has been described that connection between the x-ray detector and x-ray scanner can be detected, it also contemplated that similar techniques may be used to determine connection of an x-ray detector or x-ray scanner just to the tether.

Figure 10:
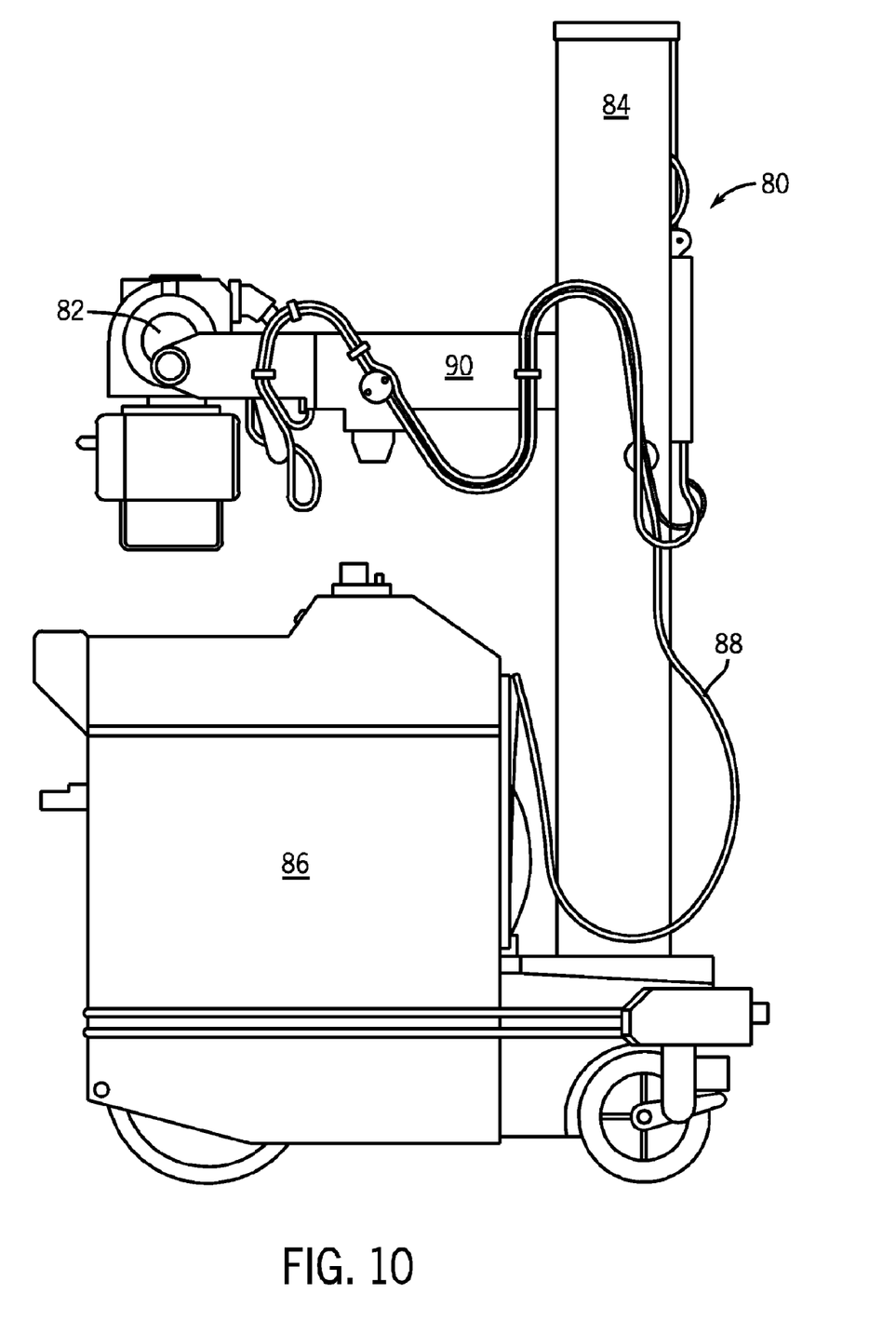
FIG. 10 is a pictorial view of an exemplary mobile x-ray imaging system.

Referring now to FIG. 10, an exemplary mobile x-ray imaging system 80 applicable with a portable x-ray detector incorporating the present invention is shown. An x-ray source 82 is mounted or otherwise secured to an end of horizontal arm 90. Arm 90 allows the x-ray source 82 to be variably positioned above a subject in such a manner so as to optimize irradiation of a particular area of interest. The x-ray source 82 is typically mounted through a gimbal-type arrangement (not shown) in column 84. In this regard, the x-ray source may be rotated vertically from a rest or park position on the mobile x-ray unit base 86 to the appropriate position above the subject in order to take an x-ray exposure of the subject. The rotational movement of column 84 is typically limited to a value of 360 degrees or less to prevent entanglement of high voltage cables 88 used to provide electrical power to the x-ray source 82. Cables 88 may be connected to a utility line source (not shown) or a battery (not shown) in the base 86 to energize the x-ray source 82 as well as other electronic components of the system 80. One skilled in the art will appreciate that system 80 may be equipped or connectable to a display unit (not shown) for the display of images captured from the imaging subject.

Therefore, the invention includes an x-ray scanning system comprising an x-ray scanner having an x-ray source configured to project x-rays at a subject to be imaged. The system includes an x-ray detector configured to detect x-rays projected from the x-ray source and attenuated by the subject and a quick-connect connection detachably linking the x-ray scanner and the x-ray detector.

The invention also includes a radiographic detector comprising a scintillator configured to convert radiographic energy to light and a detector array having a plurality of detector elements to detect light from the Scintillator. A control board is included having a plurality of electronic components to control the detector array during data acquisition and data readout. The radiographic detector further includes a quick-connect connector operationally connected to the control board and configured to detachably connect to an x-ray scanner.

The present invention further includes an x-ray control tether comprising a flexible housing extending from a first end to a second end and configured to enclose a plurality of wires, a communication wire enclosed in the flexible housing and configured to relay communication signals between an x-ray scanner and an x-ray detector, and a power wire enclosed in the flexible housing and configured to relay power supply signals between the x-ray scanner and the x-ray detector. The x-ray control tether also includes at least one quick-connect connector attached to an end of the flexible housing and connected to the communication wire and the power wire.

The present invention also includes a method of imaging a subject. The method includes the positioning an x-ray detector disconnected from an x-ray scanner in a given scan position relative to a subject to be scanned. The method further includes the steps of connecting the x-ray detector to the x-ray scanner and then acquiring radiographic data from the subject.

The present invention has been described in terms of the preferred embodiment, and it is recognized that equivalents, alternatives, and modifications, aside from those expressly stated, are possible and within the scope of the appending claims.

What is claimed is:

1. An x-ray scanning system comprising:
   an x-ray scanner and x-ray source combination having the x-ray source mounted to the x-ray scanner configured to project x-rays at a subject to be imaged;
   an x-ray detector configured to detect x-rays projected from the x-ray source and attenuated by the subject; and
   a quick-connect connection detachably linking the x-ray scanner and x-ray source combination to the x-ray detector.

2. The x-ray scanning system of claim 1 wherein the quick-connect connection comprises a single quick-connect connection point for communication lines and power lines between the x-ray scanner and x-ray source combination and the x-ray detector.

3. The x-ray scanning system of claim 1 wherein the quick-connect connection further comprises multiple in-line quick-connect connectors.

4. The x-ray scanning system of claim 1 wherein the quick-connect connection is configured to detachably link the x-ray scanner and x-ray source combination and the x-ray detector without user removal of a control panel of the x-ray scanner or the x-ray detector.

5. The x-ray scanning system of claim 1 wherein the quick-connect connection further comprises a first quick-connect connector operationally connected to a control interface of the x-ray scanner and x-ray source combination.

6. The x-ray scanning system of claim 5 wherein the quick-connect connection further comprises a second quick-connect connector operationally connected to a control board interface of the x-ray detector and engageable with the first quick-connect connector.

7. The x-ray scanning system of claim 5 wherein the first quick-connect connector is attached to an end of a control tether extending from the x-ray scanner and x-ray source combination.

8. The x-ray scanning system of claim 5 wherein the second quick-connect connector is attached to an end of a control tether extending from the x-ray detector.

9. The x-ray scanning system of claim 1 further comprising:
   a plurality of communication wires connected to the quick-connect connection and configured to transmit communication signals between the x-ray scanner and x-ray source combination and the x-ray detector; and
   a plurality of power wires connected to the quick-connect connection and configured to transmit power signals between the x-ray scanner and the x-ray detector.

10. The x-ray scanning system of claim 9 wherein the plurality of communication wires and the plurality of power wires are constructed of a copper material.

11. The x-ray scanning system of claim 1 wherein the x-ray detector further comprises:
    a scintillator configured to convert radiographic energy to light;
    a detector array having a plurality of detector elements to detect light from the scintillator; and
    a control board having a plurality of electronic components to control the detector array during data acquisition and data readout.

12. A radiographic detector comprising:
    a scintillator configured to convert radiographic energy to light;
    a detector array having a plurality of detector elements to detect light from the scintillator;
    a control board having a plurality of electronic components to control the detector array during data acquisition and data readout; and
    a quick-connect connector operationally connected to the control board and configured to detachably connect to an x-ray scanner, wherein the x-ray scanner has an x-ray source mounted thereon.

13. The radiographic detector of claim 12 wherein the quick-connect connector comprises a single quick-connect connection point between the x-ray scanner and the control board.

14. The radiographic detector of claim 12 further comprising a flexible housing to enclose the scintillator, the detector array, and the control board.

15. The radiographic detector of claim 14 wherein the quick-connect connector includes a socket mounted to an external surface of the housing and accessible without removal of a cover panel.

16. The radiographic detector of claim 14 further comprising a detector control tether operationally connecting the quick-connect connector to the control board wherein the detector control tether extends beyond an external surface of the housing.

17. The radiographic detector of claim 12 further comprising means for detachably coupling the quick-connect connector to a mating quick-connect connector.

18. The radiographic detector of claim 17 wherein the means for detachably coupling the quick-connect connector to a mating quick-connect connector comprises a threaded engagement.

19. The radiographic detector of claim 17 wherein the means for detachably coupling the quick-connect connector to a mating quick-connect connector comprises a breakaway snap-fit engagement.

20. The radiographic detector of claim 17 wherein the mating quick-connect connector is attached to an end of an x-ray scanner control tether extending from the x-ray scanner.

21. The radiographic detector of claim 12 wherein the quick-connect connector further comprises:
   a plurality of communication pins attached to communication wires and configured to transfer communication signals between the x-ray scanner and the radiographic detector; and
   a plurality of power pins attached to power wires and configured to transfer power signals between the x-ray scanner and the radiographic detector.

22. The radiographic detector of claim 21 wherein the communication wires and the power wires are made from a copper material.

23. The radiographic detector of claim 12 wherein the scintillator is configured to detect x-rays projected from the x-ray source and attenuated by a subject to be imaged.

24. An x-ray control tether system comprising:
   a flexible housing extending from a first end to a second end and configured to enclose a plurality of wires;
   a communication wire enclosed in the flexible housing and configured to relay communication signals between an x-ray scanner and an x-ray detector, the x-ray scanner having an x-ray source mounted thereon;
   a power wire enclosed in the flexible housing and configured to relay power supply signals between the x-ray scanner and the x-ray detector; and
   at least one quick-connect connector attached to an end of the flexible housing and connected to the communication wire and the power wire.

25. The x-ray control tether system of claim 24 wherein the at least one quick-connect connector is configured to detachably connect to a mating quick-connect connector operationally attached to a control interface of the x-ray scanner.

26. The x-ray control tether system of claim 24 wherein the at least one quick-connect connector is configured to detachably connect to a mating quick-connect connector operationally attached to a control interface of the x-ray detector.

27. The x-ray control tether system of claim 24 wherein the at least one quick-connect connector threadedly engages a mating quick-connect connector detachably connected thereto.

28. The x-ray control tether system of claim 24 wherein the at least one quick-connect connector snap-fittingly engages a mating quick-connect connector detachably connected thereto.

29. The x-ray control tether system of claim 24 wherein the communication wire is composed of a copper material or of fiber optic material.

30. The x-ray control tether system of claim 24 wherein the power wire is composed of a copper material.

31. The x-ray control tether system of claim 24 configured to translate imaging data signals from a flat-panel, indirect detection, digital x-ray detector.

32. A method of imaging a subject comprising the steps of:
   positioning an x-ray detector disconnected from an x-ray scanner in a given scan position relative to a subject to be scanned;
   after the positioning, connecting the x-ray detector to the x-ray scanner; and then
   acquiring radiographic data from the subject.

33. The method of claim 32 further comprising the step of disconnecting the x-ray detector from the x-ray scanner after data acquisition.

34. The method of claim 31 further comprising the step of disconnecting the x-ray detector from the x-ray scanner prior to the step of positioning.

* * * * *